United States Patent [19]

Chappelow et al.

[11] Patent Number: 5,808,108

[45] Date of Patent: Sep. 15, 1998

[54] POLYMERIC COMPOSITIONS AND COMPOSITES PREPARED FROM SPIROORTHOCARBONATES AND EPOXY MONOMERS

[76] Inventors: Cecil C. Chappelow, 12305 Cherokee La., Leawood, Kans. 66209; J. David Eick, 21 The Woodlands, Gladstone, Mo. 64119; Charles S. Pinzino, 8741 Chestnut Cir., Kansas City, Mo. 64131

[21] Appl. No.: 782,685

[22] Filed: Jan. 15, 1997

[51] Int. Cl.$^6$ ...................... C07D 319/00; C07D 327/06; C08G 59/00; A61K 6/08

[52] U.S. Cl. .............................. 549/335; 549/14; 549/15; 58/87; 58/96; 523/116; 106/35

[58] Field of Search ................................ 549/14, 15, 335; 514/433, 434, 436, 452, 453; 523/400, 116; 58/111, 87, 96; 106/35

[56] References Cited

U.S. PATENT DOCUMENTS

| | | | |
|---|---|---|---|
| 3,621,034 | 11/1971 | Fruhstorfer et al. | 549/335 |
| 3,679,707 | 7/1972 | Yoshimura et al. | 523/400 |
| 3,900,218 | 8/1975 | Miyamoto et al. | 503/205 |
| 4,368,314 | 1/1983 | Endo | 528/89 |
| 4,387,215 | 6/1983 | Bailey | 528/354 |
| 4,511,491 | 4/1985 | Ishii et al. | 549/335 |
| 4,656,294 | 4/1987 | Kanayama | 549/335 |
| 4,855,367 | 8/1989 | Flury | 525/507 |
| 4,870,193 | 9/1989 | Taguchi et al. | 549/335 |
| 4,950,771 | 8/1990 | Masumoto et al. | 549/335 |
| 5,556,896 | 9/1996 | Byerley et al. | 523/116 |

FOREIGN PATENT DOCUMENTS 64726   4/1986   Japan .

OTHER PUBLICATIONS

Bai et al, "Improvement of adhesion property of epoxy resin using oligomers made from diisocyanates and 3,9–dihyrdroxymethylene–3',9'–diethyl–1,5,7,11–tetraoxaspiro[5,5]undecane", CA123:258384, 1995.

Anderson, et al., *Silicon Compounds: Register and Review*, 5th Edition, Piscataway, N.J., p. 4.

Byerley, et al., "Expandable Matrix Monomers for Dental Composites", *J. Dent. Res.* 69:263 Abstr. No. 1233; p. 263, Mar., 1990.

Byerley, et al., "Spiro–orthocarbonates: Polymerization and Volume Change Determinations", *J. Dent. Res.* 70:527, Abstr. No 2087, p. 2087, Apr., 1991.

Byerley, et al., "Spiro–orthocarbonates: Polymerization and Volume Change Determinations", pp. 1–10, Apr., 1991.

William J. Bailey, "Matrices that Expand on Curing for High Strength Composites and Adhesives", *Materials Science & Engineering, A126*, pp. 271–279, (1990).

Bailey, et al., "Radical Ring–Opening Polymerization and Copolymerization with Expansion in Volume", *Journal of Polymer Science: Polymer Symposium 64*, pp. 17–26, (1978).

Stansbury, et al., "Evaluation of Spiro Orthocarbonate Monomers Capable of Polymerization with Expansion as Ingredients in Dental Composite Materials", *Progress in Biomedical Polymers*, pp. 133–139, 1990.

A.T. Blomquist, et al., "The Mineral Acid–catalyzed Reaction of Cyclohexene with Formaldehyde", *Acid–Catalyzed Reaction of Cyclohexene with Formaldehyde*, pp. 6025–6030, Nov. 20, 1957.

M.A. Manzhen, *International Journal of Polymeric Materials*, "Photoinitated Cationic Copolymerization of an Alicyclic Epoxy Compound and a Spiroorthocarbonate", vol. 18, at pp. 1–7 (1992).

M.A. Manzhen, *International Journal of Polymeric Materials*, "Effect of Structural Difference of Photoinitiator on Photocopolymerization of an Alicyclic Epoxy Compound and a Spiroorthocarbonate", vol. 18, at pp. 189–195 (1992).

DeWolfe, "Synthesis of Carboxylic and Carbonic Ortho Esters", pp. 153–172, Mar., 1974.

Pingsheng He; W. Zhou; G. Wang; C. Pan; and R. Wu, *Chinese Journal of Polymer Science*, "Study on Copolymer Epoxy Resin Matrix without Shrinkage: Part 1 Volume Change During Cure Processes", vol. 6, at pp. 30–35 (1988).

Pingsheng He and Zhiqiang Zhou, *Journal of Material Science*, "Epoxy Resin Copolymer with Zero Shrinkage, Part II Thermal and Mechanical Properties", vol. 26, at pp. 3792–3796 (1991).

Pingsheng He, et al., *Journal of Material Science*, "An Epoxy Resin Copolymer with Zero Shrinkage, Part I Volume Change on Cure", vol. 24, at pp. 1528–1532 (1989).

He et al., *Chem. Abs.*, 1099, Ab. #74,464 (1989).

*Primary Examiner*—Deborah C. Lambkin
*Attorney, Agent, or Firm*—Shook, Hardy & Bacon L.L.P.

[57]   ABSTRACT

Polymeric compositions are provided which are the reaction product of spiroorthocarbonates and epoxy resins and undergo reduced bulk polymerization shrinkage. The spiroorthocarbonates are of the general formula:

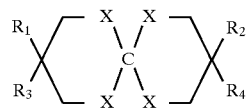

wherein
  X=O or S;
  $R_1$ and $R_2$ are independently selected from the group consisting of H, alkyl, aryl, substituted alkyl, and substituted aryl;
  $R_3$ and $R_4$=—$(CH_2)_n$—O—$R_5$;
  n=1 or 2;
  $R_5$=alkyl, aryl, substituted aryl, substituted alkyl,

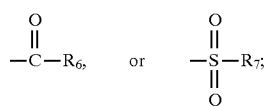

$R_6$=H, alkyl, aryl, substituted alkyl, or substituted aryl; and
  $R_7$=alkyl, aryl, substituted alkyl, or substituted aryl.

11 Claims, No Drawings

POLYMERIC COMPOSITIONS AND COMPOSITES PREPARED FROM SPIROORTHOCARBONATES AND EPOXY MONOMERS

BACKGROUND OF THE INVENTION

The government has certain rights in this invention.

This invention relates in general to compositions of matter and, more particularly, to spiroorthocarbonates and the use thereof in reducing the shrinkage of polymeric compositions. The polymeric compositions are useful as dental composites.

The shrinkage during polymerization of many types of monomers makes those monomers generally unsuited for use in numerous applications, including as strain-free composites, high-strength adhesives, and precision castings. As an example, when such monomers are used in composites which include high-strength fibers, the polymeric matrix is subject to failure when the polymer shrinks and pulls away from the fibers. Failure of the composite can also occur when the matrix ruptures as a result of voids or micro cracks which form in the matrix during polymerization shrinkage.

Polymeric matrices commonly employed in dental composites are based on 2,2'-bis[4-(2-hydroxy-3-methacryloyloxypropoxy)]phenyl propane (BisGMA). A significant problem associated with the use of this monomer in dental applications is the shrinkage which occurs as the monomer is polymerized. The BisGMA monomer itself typically experiences a shrinkage of approximately 5% and, when a low viscosity reactive diluent is combined with the monomer, the shrinkage may average as much as 7.9%. The adverse effects of such shrinkage are believed to include increased postoperative sensitivity, the formation of marginal gaps between the dental restoration and the cavity wall, cracking of the restoration, and microleakage and potential failure of the restoration.

The discovery that spiroorthocarbonates undergo reduced polymerization contraction has led to the suggestion of their use in reinforced composites, including as dental composites. Spiroorthocarbonates are esters of orthocarboxylic acid and have four oxygen atoms bonded to a single carbon atom, with the carbon atom being common to two ring systems. The expansion of the spiroorthocarbonates on polymerization is attributed to a double spiro-cyclic ring opening of the spiroorthocarbonates, resulting in the breaking of two covalent bonds to form one new bond.

Initial attempts to form a homogeneous polymer matrix from certain spiroorthocarbonates and BisGMA resin mixtures proved unsuccessful because of the incomplete polymerization of the spiroorthocarbonates. Thompson et al., J. Dental Research 58:15221532 (1979). More recent studies demonstrated that homogeneous mixtures of other spiroorthocarbonates and BisGMA could be obtained. Stansbury, J. Dental Research 70:527; Abstract No. 2088 (1991). However, the presence of a vinyl functionality in these spiroorthocarbonate monomers, in combination with the unsaturation of the BisGMA monomers, resulted in a polymerization shrinkage of 2.4%, making the polymer unsuited for those application requiring slight polymer expansion or minimal shrinkage.

The photocationic-initiated expansion polymerization of alicyclic spiroorthocarbonate monomers and the potential use of the resulting polymers as dental composites have been previously reported by the present inventors, with others. Byerley et al., Dent. Mater. 8:345–350 (1992). The specific spiroorthocarbonates identified by Byerley et al. include cis/cis, cis/trans, and trans/trans configurational isomers of 2,3,8,9-di(tetramethylene)1,5,7,11-tetraoxaspiro-[5.5] undecane. The trans/trans isomer has the following formula:

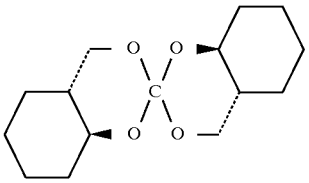

These spiroorthocarbonates were determined to undergo an expansion of 3.5% during homopolymerization and demonstrated acceptable cytotoxicity and genotoxicity properties, making them promising candidates as composite resin matrix materials.

The present inventors, with others, have also previously reported on the preparation of a copolymer of an alicyclic spiroorthocarbonate and an unidentified monofunctional epoxide, with the observation that there were no indications of the formation of small ring compounds as polymerization by-products. Byerley et al., J. Dental Research 69:263; Abstract No. 1233 (1990). The copolymerization of trans/trans-2,3,8,9di(tetramethylene)-1,5,7,11-tetraoxaspiro-[5,5] undecane and commercially available multifunctional epoxides was also disclosed in a paper presented by Byerley et al. However, no physical or mechanical properties, including percentage shrinkage, of the copolymer compositions were disclosed.

The combination of other spiroorthocarbonates with epoxy resins have produced copolymer composite matrices exhibiting decreased water permeation, increased toughness, and significantly decreased polymerization shrinkage. In one example, an expansion of 1.6% was observed when 24% of a dinorbornene spiroorthocarbonate was copolymerized with a diglycidyl ether of bisphenol A. Piggott et al., 31st International SAMPE Symposium 541–550 (1986).

It has also been reported that homopolymerization of an epoxy monomer at ambient temperature would result in very minimal shrinkage. Fish et al., Plastic Technology, 1:28–32 (1961).

One problem which has resulted from the use of many types of spiroorthocarbonates in combination with epoxies to form polymeric compositions is the inability to achieve complete polymerization of both the spiroorthocarbonates and the epoxies and their resulting mixture. It is known to use polyols in combination with epoxies to enhance the degree of polymerization to the epoxies by extending the gel state. However, polymerization of the epoxy component may still occur at a faster rate than the ring opening polymerization of many spiroorthocarbonates and may result in unreacted spiroorthocarbonates becoming trapped in the polymer matrix. If signification amounts of the spiroorthocarbonates are trapped and are unable to undergo ring operating reactions and polymerization, the desired expansion of the polymeric composition will not be obtained.

Despite the advances resulting from the above-noted investigations of the use of spiroorthocarbonates as composite materials, a need still exists for a spiroorthocarbonate copolymer capable of yielding a hard, non-shrinking matrix resin suitable for formulating dental and other composites.

SUMMARY OF THE INVENTION

It is a primary object of this invention to provide a new class of spiroorthocarbonates useful with epoxies in polymeric compositions that possesses the mechanical and physical properties necessary to allow the composition to be used as a composite material, including as a dental composite matrix.

It is also an object of this invention to provide a spiroorthocarbonate and epoxy polymeric composition that has a reduced polymerization shrinkage and water sorption in comparison to the epoxy polymer itself so that the polymeric composition can be used in those applications in which the epoxy polymer cannot be used.

It is another object of this invention to provide a new class of spiroorthocarbonates which are sufficiently soluble and miscible in epoxies to allow high loadings of the spiroorthocarbonates and reduced shrinkage of polymeric compositions formed by (co)polymerization of the spiroorthocarbonates and epoxies.

It is a further object of this invention to provide a new class of spiroorthocarbonates which undergo ring opening reactions and polymerization at a comparable rate to the polymerization of epoxies so that more complete (co) polymerization of a mixture of the spiroorthocarbonates and epoxies may occur with resulting reduction of shrinkage and rigidity of the resulting polymeric composition.

It is still another object of this invention to provide a dental composite having a tensile strength and modulus of elasticity comparable with that of conventional dental composites but having negligible shrinkage during polymerization so that the composite is less likely to fail as a result of expansion or contraction during polymerization.

To accomplish these and other related objects of the invention, in one aspect the invention is directed to spiroorthocarbonates having the formula I:

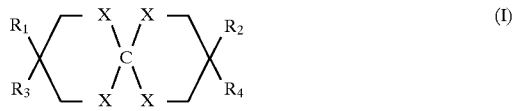

wherein
X=O or S;
$R_1$ and $R_2$ are independently selected from the group consisting of H, alkyl, aryl, substituted alkyl, and substituted aryl;
$R_3$ and $R_4$=—$(CH_2)_n$—O—$R_5$;
n=1 or 2;
$R_5$=alkyl, aryl, substituted aryl, substituted alkyl,

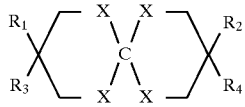

$R_6$=H, alkyl, aryl, substituted alkyl, or substituted aryl; and
$R_7$=alkyl, aryl, substituted alkyl, or substituted aryl.
As used herein, alkyl refers to groups having 1 to 12 carbon atoms, preferably 1 to 10 carbon atoms, and more preferably 1 to 8 carbon atoms.

In another aspect, the invention is directed to a polymeric composition comprising a reaction product of one or more spiroorthocarbonates of formula I, a polymerizable epoxy resin, and a hydroxyl containing material, preferably a polyol. A photoinitiator such as (4-octyloxyphenyl) phenyliodonium hexafluoroantimonate or other aryliodonium salt can be included to catalyze the polymerization. A photosensitizer can also be included to extend the spectral sensitivity of the photoinitiator to longer wavelengths. The polymeric composition is particular useful as a dental composite, with the reaction product forming a matrix in which nonreactive dental fillers may be dispersed.

DESCRIPTION OF THE PREFERRED EMBODIMENTS

The spiroorthocarbonates of the present invention are represented by the following general formula I:

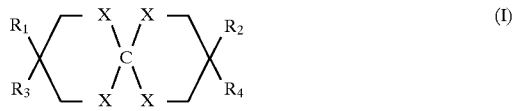

wherein
X=O or S;
$R_1$ and $R_2$ are independently selected from the group consisting of H, alkyl, aryl, substituted alkyl, and substituted aryl;
$R_3$ and $R_4$=—$(CH_2)_n$—O—$R_5$;
n=1 or 2;
$R_5$=alkyl, aryl, substituted aryl, substituted alkyl,

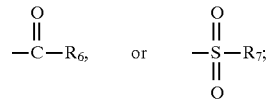

$R_6$=H, alkyl, aryl, substituted alkyl, or substituted aryl; and
$R_7$=alkyl, aryl, substituted alkyl, or substituted aryl.
As used herein, alkyl refers to groups having 1 to 12 carbon atoms, preferably 1 to 10 carbon atoms, and more preferably 1 to 8 carbon atoms. Representative examples of spiroorthocarbonates of formula I include: 3,9-diacetoxymethyl-3, 9-diethyl-1,5,7,11-tetraoxaspiro[5.5]undecane (DAMDE); 3,9-diacetoxymethyl-3,9-dimethyl-1,5,7,11-tetraoxaspiro [5.5]undecane (DAMDM); 3,9-diethyl-3,9-dipropionyloxymethyl-1,5,7,11-tetraoxaspiro[5.5]undecane (DEDPM); 3,9-diacetoxymethyl-3,9-diphenyl-1,5,7,11-tetraoxaspiro[5.5]undecane (DAMDP); 3,9-dibenzyloxymethyl-3,9-dimethyl-1,5,7,11-tetraoxaspiro [5.5]undecane (DBOMDM); 3,9-diethyl-3,9-di (isopropylcarbamoyloxymethyl)-1,5,7,11-tetraoxaspiro[5.5] undecane (DEDPCM); 3,9-diethyl-3,9-di(n-propylsulfonyloxymethyl)-1,5,7,11-tetraoxaspiro[5.5] undecane (DEDPSM); and 3,9-diethyl-3,9-di(4-tolylcarbamoyloxymethyl)-1,5,7,11-tetraoxaspiro[5.5] undecane (DEDTCM). The structural and optical isomers of these compounds may be used individually or in combination.

The spiroorthocarbonates can be prepared by transesterification of tetraalkylorthocarbonates such as tetraethylorthocarbonate or tetramethylorthocarbonate and the corresponding diol using an aromatic hydrocarbon solvent such as toluene or xylene in the presence of a catalytic amount of an organic acid such as p-toluene sulfonic acid. The reaction is driven to completion by removal of the alcohol and is purified by distillation or chromatography and/or recrystallization. The spiroorthocarbonate compounds can also be prepared by other reactions involving thiolphosgenation and organotin intermediates. See generally, R. K. Sadhir & R. M. Luck, *Expanding Monomers: Synthesis, Characterization and Applications*, CRC Press, Boca Raton, Fla. (1992).

The spiroorthocarbonates of formula I expand as they undergo ring-opening reactions and are particularly suited for use in reducing shrinkage of polymeric compositions of the present invention. The polymeric compositions comprise a cationic initiated reaction product of a mixture of a spiroorthocarbonate of formula I and a cationically polymerizable epoxy resin. Optionally, but preferably, the mixture includes a hydroxyl-containing material soluble in the epoxy resin and which serves to enhance the degree of polymerization of the epoxy resin by extending the gel state during polymerization. The three primary components of the reaction mixture, i.e., the spiroorthocarbonates, epoxy resins and hydroxyl-containing material, should be soluble in each other to achieve the desired polymeric compositions.

The amount of hydroxyl-containing material used in the compositions of the invention may vary over broad ranges, depending upon factors such as the compatibility of the hydroxyl-containing material with the epoxy resin, the equivalent weight and functionality of the hydroxyl-containing material, the physical properties desired in the final cured composition, the desired speed of photocure, and the like. The amount of hydroxyl-containing material should be selected to provide the desired flexibility or rigidity for the resulting polymeric composition. In general, as more hydroxyl-containing material is added to the mixture, more complete polymerization occurs. If insufficient amounts of hydroxyl-containing material are added, the resulting composition may be too rigid or may have other undesirable properties as a result of incomplete polymerization. If too much hydroxyl-containing material is added, it may cause too much flexibility in the polymer composition. Suitable ratios of epoxy to hydroxyl-containing material include 100:0 to 65:35, preferably 95:5 to 70:30, and more preferably 90:10 to 80:20.

In dental applications, the spiroorthocarbonate must be selected in combination with the epoxy resin so that the resulting polymeric composition undergoes a negligible shrinkage during polymerization. In general, increasing amounts of spiroorthocarbonates in the reaction mixture cause decreasing shrinkage of the polymeric composition. High loadings of spiroorthocarbonates are thus desirable in the reaction mixtures of the present invention. Suitable ratios of the epoxy/hydroxyl-containing material to the spiroorthocarbonates range from 90:10 to 40:60 wt % and more preferably from 80:20 to 50:50 wt %.

The cationically polymerizable epoxy resins useful in the compositions of the present invention are chosen to provide a low viscosity fluid reaction mass in which the spiroorthocarbonates of formula I are soluble, including at loading concentrations of spiroorthocarbonates of up to or exceeding 90% by weight. It should be noted that it is not presently known whether the reaction of the spiroorthocarbonate and epoxy forms a copolymer, an interpenetrating polymer network or some other polymeric structure. The epoxy resin should also cure rapidly at ambient temperature.

The cationically polymerizable epoxy resins comprise organic compounds having an oxirane ring, i.e.,

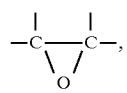

polymerizable by ring opening. Such materials are broadly referred to as epoxides and include monomeric epoxy compounds and epoxides of the polymeric type and can be aliphatic, cycloaliphatic, aromatic or heterocyclic. These materials generally have, on the average, at least one polymerizable epoxy group per molecule, and preferably at least about 1.5 polymerizable epoxy groups per molecule. The polymeric epoxides include linear polymers having terminal epoxy groups (e.g., a diglycidyl ether of a polyoxyalkylene glycol), polymers having skeletal oxirane units (e.g, polybutadiene polyepoxide), and polymers having pendent epoxy groups (e.g., a glycidyl methacrylate polymer or copolymer). The epoxides may be pure compounds or may be mixtures containing one, two, or more epoxy groups per molecule. The "average" number of epoxy groups per molecule is determined by dividing the total number of epoxy groups in epoxy-containing material by the total number of epoxy molecules present.

These epoxy-containing materials may vary from low molecular weight monomeric materials to high molecular weight polymers and may vary greatly in the nature of their backbone and substituent groups. For example, the backbone may be of any type and substituent groups thereon can be any group that does not substantially interfere with cationic cure at room temperature. Illustrative of permissible substituent groups include halogens, ester groups, ethers, sulfonate groups, siloxane groups, nitro groups, phosphate groups and the like. The molecular weight of the epoxy-containing materials may vary from about 58 to about 100,000 or more.

Useful epoxy-containing materials include those which contain cyclohexene oxide groups such as the epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl) adipate. For a detailed list of useful epoxides of this nature, reference is made to U.S. Pat. No. 3,117,099, incorporated herein by reference.

Further epoxy-containing materials which are particularly useful in the practice of this invention include glycidyl ether monomers of the formula

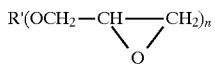

where R' is alkyl or aryl and n is an integer of 1 to 6. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)-propane). Further examples of epoxides of this type which can be used in the practice of this invention are described in U.S. Pat. No. 3,018,262, incorporated herein by reference, and in "Handbook of Epoxy Resins" by Lee and Neville, McGraw-Hill Book Co., New York (1967) and in "Epoxy Resins-Chemistry & Technology," edited by C. A. May, 2d edition (1988).

There are a host of commercially available epoxy resins which can be used in this invention. In particular, epoxides which are readily available include octadecylene oxide, epichlorohydrin, styrene oxide, vinyl cyclohexene oxide, glycidol, glycidylmethacrylate, diglycidyl ether of Bisphenol A (e.g., those available under the trade designations "Epon 828", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexene carboxylate (e.g., "ERL-4221" or "UVR 6110" from Union Carbide Corp.), 3,4-epoxycyclohexanemethyl-3,4-epoxycyclohexene carboxylate (e.g., "UVR 6105" from Union Carbide Corp.), 3,4-epoxy-6-methylcyclohexylmethyl-3,4-epoxy-6-methyl-cyclohexene carboxylate (e.g., "ERL-4201" from Union Carbide Corp.), bis(3,4-epoxy-6-methylcyclohexylmethyl) adipate (e.g., "ERL-4289" from Union Carbide Corp.), bis(2,3-epoxycyclopentyl) ether (e.g., "ERL-0400" from Union Carbide Corp.), aliphatic epoxy modified with polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from Dow Chemical Co.), 1,4-butanediol diglycidyl ether of phenolformaldehyde novolak (e.g., "DEN-431" and "DEN-438" from Dow Chemical Co.), and resorcinol diglycidyl ether (e.g., "Kopoxite" from Koppers Company, Inc.), bis(3,4-epoxycyclohexyl) adipate (e.g., "ERL-4299" or "UVR-6128", from Union Carbide Corp.), 2-(3,4-epoxycyclohexyl-5,5-spiro-3,4-epoxy) cyclohexane-meta-dioxane (e.g., "ERL-4234" from Union Carbide Corp.), vinylcyclohexene monoxide (from Union Carbide Corp.), 1,2-epoxyhexadecane (e.g., "UVR-6216" from Union Carbide Corp.), alkyl glycidyl ethers such as alkyl $C_8$–$C_{10}$ glycidyl ether (e.g., "HELOXY Modifier 7" from Shell Chemical Co.), alkyl $C_{12}$–$C_{14}$ glycidyl ether (e.g., "HELOXY Modifier 8" from Shell Chemical Co.), butyl glycidyl ether (e.g., "HELOXY Modifier 61" from Shell Chemical Co.), cresyl glycidyl ether (e.g., "HELOXY Modifier 62" from Shell Chemical Co.), p-tert butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1138" or "GY-281" from Ciba Geigy Corp.), 9,9-bis[4-(2, 3-epoxypropoxy)-phenyl]fluorenone (e.g., "Epon 1079" from Shell Chemical Co.).

Still other epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins are well known and contain such epoxides as epichlorohydrins, e.g., epichlorohydrin; alkylene oxides, e.g., propylene oxide, styrene oxide, alkenyl oxides, e.g., butadiene oxide; glycidyl esters, e.g., ethyl glycidate.

The polymers of the epoxy resin may optionally contain other functionalities that do not substantially interfere with cationic cure at room temperature.

Blends of various epoxy-containing materials are particularly contemplated in this invention. Examples of such blends include two or more molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical nature, such as aliphatic and aromatic, or functionality, such as polar and non-polar. Other cationically polymerizable polymers may additionally be incorporated.

Particularly preferred epoxy resins are vinylcyclohexene dioxide (ERL-4206), bis(3,4-epoxycyclohexylmethyleneoxy)adipate (ERL-4299), and 3,4-epoxycyclohexanemethyl-3,4-epoxycyclohexane carboxylate (UVR-6105).

The hydroxyl-containing material which is used in the present invention may be any liquid or solid organic material having hydroxyl functionally of at least 1, and preferably at least 2, i.e., a polyol.

Preferably the hydroxyl-containing material contains two or more primary or secondary aliphatic hydroxyl groups (i.e., the hydroxyl group is bonded directly to a non-aromatic carbon atom). The hydroxyl group may be terminally situated, or they may be pendent from a polymer or copolymer. The molecular weight of the hydroxyl-containing organic material may vary from very low (e.g., 32) to very high (e.g., one million or more). Suitable hydroxyl-containing materials may have low molecular weights, i.e., from about 32–200, intermediate molecular weight, i.e., from about 200–10,000, or high molecular weight, i.e. above about 10,000. As used herein, all molecular weights are weight average molecular weights.

The hydroxyl-containing material may optionally contain other functionalities that do not substantially interfere with cationic cure at room temperature. Thus, the hydroxyl-containing materials may optionally be nonaromatic in nature or may comprise aromatic functionality. The hydroxyl-containing material may optionally contain heteroatoms in the backbone of the molecule, such as nitrogen, oxygen, sulfur, and the like, provided that the ultimate hydroxyl-containing material does not substantially interfere with cationic cure at room temperature. The hydroxyl-containing material may, for example, be selected from naturally occurring or synthetically prepared cellulosic materials. Of course, the hydroxyl-containing material is also substantially free of groups which may be thermally or photolytically unstable; that is, the material will not decompose or liberate volatile components at temperatures below about 100° C. or in the presence of actinic light which may be encountered during the desired curing conditions for the photocopolymerizable composition.

Representative examples of suitable hydroxyl-containing materials having a hydroxyl functionality of 1 include alkanols, monoalkyl ethers of polyoxyalkyleneglycols, monoalkyl ethers of alkylene-glycols, and others known to the art.

Representative examples of useful monomeric polyhydroxy organic materials include alkylene glycols (e.g., 1,2-ethanediol; 1,4-butanediol; 1,6-hexanediol; 1,8-octanediol; 2-ethyl-1,6-hexanediol; bis(hydroxymethyl)cyclohexane; 1,18-dihydroxyoctadecane; 3-chloro-1,2-propanediol; polyhydroxyalkanes (e.g., glycerine, tri-methylolethane, pentaerytiritol, sorbitol) and other polyhydroxy compounds such as N, N-bis(hydroxyethyl)benzamide; 2-butyne-1, 4-diol; 4,4'-bid(hydroxymethyl)diphenylsulfone; castor oil; and the like.

Representative examples of useful polymeric hydroxyl-containing materials include a polyoxyethylene and polyoxypropylene glycols, and particularly the polyoxyethylene and polyoxypropylene glycol diols and triols of molecular weights from about 200 to about 10,000 corresponding to equivalent eight of 100 to 5000 for the diols or 70 to 3300 for triols; polytetramethylene ether glycols (polytetrahydrofuran "poly THF") of varying molecular weight; copolymers of hydroxypropyl and hydroxyethyl acrylates and methacrylates with other free radical-polymerizable monomers such as acrylate esters, vinyl halides, or styrene; copolymers containing pendent hydroxy groups formed by hydrolysis or partial hydrolysis of vinyl acetate copolymers, polyvinylacetal resins containing pendent hydroxyl groups; modified cellulose polymers such as hydroxyethylated and hydroxypropylated cellulose; hydroxy-terminated polyesters; hydroxy-terminated polylactones, and particularly the polyeaprolactones; fluorinated polyoxyethylene or polyoxypropylene glycols; and hydroxy-terminated polyalkadienes.

Useful commercially available hydroxyl-containing materials include the "Terathane" series (available from du Pont de Nemours) of polytetramethylene ether glycols such as "Terathane" 650, 1000, 2000 and 2900; "PeP" series (available from Wyandotte Chemicals Corporation) of polyoxyalkylene tetrols having secondary hydroxyl groups such as "PeP" 450, 550 and 650; "Butvar" series (available from Monsanto Chemical Company) of polyvinylacetal resins such as "Butvar" B-72A, B-73, B-76, B-90 and B-98; and "Formvar" 7/70, 12/85, 7/95S, 7/95E, 15/95S and 15/95E; "Tone" series (available from Union Carbide) of polycaprolactone polyols such as "Tone" 0200, 0210, 0230, 0240, 0300; "Paraplex U-148" (available from Rohm and Haas), and aliphatic polyester diol; "Multron" R series (available from Mobay Chemical Co.) of saturated polyester polyols such as "Multron" R-2, R-12A, R-16, R-18, R-38, R-68 and R-74; "Klucel E" (available from Hercules Inc.) a hydroxypropylated cellulose having an equivalent weight of approximately 100; and "Alcohol Soluble Butyrate" (available from Eastman Kodak) a cellulose acetate butyrate ester having a hydroxyl equivalent weight of approximately 400; polyether polyols such as polypropylene glycol diol (e.g., "Arcol PPG-425", "Arcol PPG-725", "Arcol PPG-1025", "Arcol PPG-2025", "Arcol PPG-3025", "Arcol PPG-4025" from ARCO Chemical Co.); polypropylene glycol triol (e.g., "Arcol LT-28", "Arcol LHT 112", "Arcol LHT 240", "Arcol LG-56", "Arcol LG-168", "Arcol LG-650" from ARCO Chemical Co.); ethylene oxide capped polyoxypropylene triol or diol (e.g., "Arcol 11-27", "Arcol 11-34", "Arcol E-351", "Arcol E-452", "Arcol E-785", "Arcol E-786" from ARCO Chemical Co.); propylene oxide or ethylene oxide-based polyols (e.g., "Voranol" polyether polyols such as "Voranol 230-056", "Voranol 220 series", "Voranol 230 series", "Voranol 240 series" from the Dow Chemical Co.).

The amount of hydroxyl-containing organic material used in the compositions of the invention may vary over broad ranges, depending upon factors such as the compatibility of the hydroxyl-containing material with the epoxide, the equivalent weight and functionality of the hydroxyl-containing material, the physical properties desired in the final cured composition, the desired speed of photocure, and the like. In general, the hydroxyl-containing material may be present in an amount up to approximately 40% by weight based on the total weight of the epoxy/hydroxyl mixtures, more preferably 5 to 30% by weight, and most preferably 10 to 20% by weight.

Blends of various hydroxyl-containing materials are particularly contemplated in this invention. Examples of such blends include two or more molecular weight distributions of hydroxyl-containing compounds, such as low molecular weight below 200), intermediate molecular weight (about 200 to 10,000) and higher molecular weight (above about 10,000). Alternatively or additionally, the hydroxyl-containing material may contain a blend of hydroxyl-containing materials having different chemical nature, such as aliphatic and aromatic, or functionality, such as polar and non-polar. As an additional example, one may use mixtures of two or more poly-functional hydroxy materials or one or more mono-functional hydroxy materials with polyfunctional hydroxy materials.

Preferred hydroxyl-containing materials include 2-oxepanone, polymer with 2,2-oxybisethanol (Union Carbide "Tone 201:), 2-oxepanone, polymer with 2-ethyl-2-(hydroxymethyl)-1,3-propane diol (union Carbide "Tone 301"), and particularly preferred are 1,4-cyclohexane dimethanol (Aldrich 12, 559-8), tri(ethylene glycol( (Aldrich 20, 236-3).

Polymerization of the spiroorthocarbonate and epoxy mixture can be initiated by any suitable catalyst, preferably those which will cause cationic rather than free radical initiation of the polymerization. Preferred photoinitiators are aromatic iodonium complex salts of the formula:

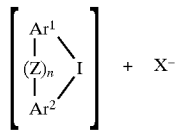

where $Ar^1$ and $Ar^2$ are aromatic groups having 4 to 20 carbon atoms and are selected from the group consisting of phenyl, thienyl, furanyl and pyrazolyl groups; Z is selected from the group consisting of oxygen; sulfur;

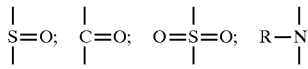

where R is aryl (of 6 to 20 carbons, such as phenyl) or acyl (of 2 to 20 carbons, such as acetyl, benzoyl, and the like); a carbon-to-carbon bond; or

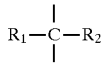

where $R_1$ and $R_2$ are selected from hydrogen, alkyl radicals of 1 to 4 carbons, and alkenyl radicals of 2 to 4 carbons; and n is zero or 1; and wherein X is a halogen-containing complex anion selected from tetrafluoroborate, hexafluorophosphate, hexafluoroarsenate, and hexafluoroantimonate.

The aromatic iodonium cations are stable and are well known and recognized in the art. See for example, U.S. Pat. Nos. 3,565,906; 3,712,920; 3,759,989; and 3,763,187; F. Beringer, et al., Diaryliodonium Sales IX, J. Am. Chem. Soc. 81,342–51 (1959) and F. Beringer, et al., Diaryliodonium Salts XXIII, J. Chem. Soc. 1964, 442–51; F. Beringer, et al., Iodonium Salts Containing Heterocyclic Iodine, J. Org. Chem. 30, 1141–8 (1965).

Representative $Ar_1$ and $Ar_2$ groups are aromatic groups having 4 to 20 carbon atoms selected from phenyl, thienyl, furanyl, and pyrazolyl groups. These aromatic groups may optionally have one or more fused benzo rings (e.g., naphthyl and the like; benzothienyl; dibenzothienyl; benzofuranyl, dibenzofuranyl; and the like). Such aromatic groups may also be substituted, if desired, by one or more of the following non-basic groups which are essentially non-reactive with epoxide and hydroxy: halogen, nitro, N-arylanilino groups, ester groups (e.g., alkoxycarbonyl such as methoxycarbonyl and ethoxycarbonyl, phenoxycarbonyl), sulfo ester groups (e.g., alkoxylsulfonyl such as methoxysulfonyl and butoxysulfonyl, phenoxysulfonyl, and the like), amido groups (e.g., acetamido, butyramido, ethylsulfonamido, and the like), carbamyl groups (e.g., carbamyl, N-alkylcarbamyl, N-phenylcarbamyl, and the like), sulfamyl groups (e.g., sulfamyl, N-alkylsulfamyl, N,N-dialkylsulfamyl, N-phenylsulfamyl, and the like), alkoxy groups (e.g., methoxy, ethoxy, butoxy, and the like), aryl groups (e.g., phenyl), alkyl groups (e.g., methyl, ethyl, butyl, and the like), aryloxy groups (e.g., phenoxy) alkylsulfonyl (e.g., methylsulfonyl, ethylsulfonyl, and the like), arylsulfonyl groups (e.g., phenylsulfonyl groups), perfluoroalkyl groups (e.g., trifluoromethyl, perfluoroethyl, and the like), and perfluoroalkylsulfonyl groups (e.g., trifluoromethylsulfonyl, perfluorobutylsulfonyl, and the like).

Suitable examples of the aromatic iodonium complex salt photoinitiators include: diphenyliodonium tetrafluoroborate; di(4-methylphenyl)iodonium tetrafluoroborate; phenyl-4-methylphenyliodonium tetrafluoroborate; di(4-heptylphenyl)iodium tetrafluoroborate; di(3-nitrophenyl) iodonium hexafluorophosphate; di(4-chlorophenyl) iodonium hexafluorophosphate; di(naphthyl)iodonium tetrafluoroborate; di(4-trifluoromethylphenyl)iodonium tetrafluoroborate; diphenliodonium hexafluorophosphate; diphenyliodonium hexafluoroarsenate; di(4-phenoxyphenyl)iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; (4-octyloxyphenyl)phenyliodonium hexafluoroantimonate; 2,2'-diphenyliodonium tetrafluoroborate; di(2,4-dichlorophenyl)iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; and di(2-benzothienyl)iodonium hexafluorophosphate.

Of the aromatic iodonium complex salts which are suitable for use in the compositions of the invention the preferred salts are the diaryliodonium hexafluorophosphate and the diaryliodonium hexafluoroantimonate. These salts are preferred because, in general, they are more thermally stable, promote faster reaction, and are more soluble in inert organic solvents than are other aromatic iodonium salts of complex ions.

The aromatic iodonium complex salts may be prepared by metathesis of corresponding aromatic iodonium simple salts (such as, for example, the diphenyliodonium bisulfate) in accordance with the teachings of Beringer, et al., J. Am. Chem. Soc. 81,342 (1959). Thus, for examples, the complex salt diphenyliodonium tetrafluoroborate is prepared by the addition at 60° C. of an aqueous solution containing 29.2 g (150 millimoles) silver fluoroborate, 2 g fluoroboric acid, and 0.5 g phosphorous acid in about 30 ml of water to a solution of 44 g (139 millimoles) of diphenyliodonium chloride. The silver halide that precipitates is filtered off and the filtrate concentrated to yield diphenyliodonium fluoroborate which may be purified by recrystallization.

The aromatic iodonium simple salts may be prepared in accordance with Beringer et al., above, by various methods including (1) coupling of two aromatic compounds with iodyl sulfate in sulfuric acid, (2) coupling of two aromatic compounds with an iodate in acetic acid-acetic anhydride-sulfuric acid, (3) coupling of two aromatic compounds with an iodine acylate in the presence of an acid, and (4) condensation of an iodoso compound, an iodoso diacetate, or an iodoxy compound with another aromatic compound in the presence of an acid. Diphenyliodonium bisulfate is prepared by method (3), for example, by the addition over a period of eight hours at below 5° C. of a mixture of 35 ml of conc. sulfuric acid and 50 ml of acetic anhydride to a well-stirred mixture of 55.5 ml of benzene, 50 ml of acetic anhydride, and 53.5 g. of potassium iodate. The mixture is stirred for an additional four hours at 0° to 5° C. and at room temperature for 48 hours and treated with 300 ml of diethyl ether. On concentration, crude diphenyliodonium bisulfate precipitates. If desired, it may be purified by recrystallization.

The diaryl iodonium salt is preferably present in the composition in amounts between about 0.01–10% by weight, more preferably between about 0.02–5% by weight, and most preferably between about 0.05–4% by weight.

A photosensitizer can be used to extend the spectral sensitivity of the photoinitiator to longer wavelengths. Desirably, the photoinitiator should be sensitized to the visible spectrum to allow the polymerization to be initiated at room temperature using visible light. The visible light sensitizer is an alpha-dicarbonyl compound having an extinction coefficient less than about 1000. Preferably, the visible light sensitizer is an alpha-diketone having an extinction coefficient less than about 1000.

A sensitizer is selected based in part upon shelf stability considerations. Accordingly, selection of a particular sensitizer may depend to some extent upon the particular epoxy, hydroxy-containing material and iodonium salt chosen.

Sensitizers useful in the present compositions have an extinction coefficient below about 1000 more preferably below about 200, and most preferably below about 150 Im$^{-1}$ cm$^{-1}$, at the desired wavelength of irradiation for photopolymerization.

By way of example, a preferred class of alpha-dicarbonyl sensitizers has the formula:

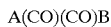

A(CO)(CO)B where A and B can be the same of different and can be hydrogen or substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Examples of particularly preferred visible light sensitizers include camphorquinone; 2-chlorothioxanthan-9-one; glyoxal; biacetyl; 3,3,6,6-tetramethylcyclohexanedione; 3,3,7,7-tetramethyl-1,2-cycloheptanedione;3,3,8,8-tetramethyl-1,2-cyclooctanedione;3,3,18,18-tetramethyl-1,2-cyclooctadecanedione; dipivaloyl; benzil; hydroxybenzil; 2,3-butanedione; 2,3-pentanedione; 2,3-hexanedione; 3,4-hexanedione; 2,3-heptanedione; 3,4-heptanedione; 2,3-octanedione; 4,5-octanedione; and 1,2-cyclohexanedione.

The visible light sensitizer is preferably present in the composition in amounts between about 0.01–10% by weight, more preferably between about 0.02–5% by weight, and most preferably between about 0.05–4% by weights.

The photopolymerizable compositions of the invention are prepared by simply admixing, under "safe light" conditions, the components of the inventive compositions. Suitable inert solvents may be employed if desired when effecting this mixture. Examples of suitable solvents are acetone and acetonitrile, and includes any solvent which does not react appreciably with the components of the inventive compositions. A liquid material to be polymerized may be used as a solvent for another liquid or solid material to be polymerized. Solventless compositions can be prepared by simply dissolving the aromatic iodonium complex salt and sensitizer in the epoxy resin or hydroxyl-containing material with or without the use of mild heating.

Dental applications particularly benefit from the unique compositions of the present invention. Until now, acrylate and methacrylate chemistry has been used extensively for adhesive and restorative dental compositions. This chemistry advantageously can be cured with visible light using photoinitiator systems. However, this chemistry has the disadvantage of a relatively high degree of shrinkage during the polymerization process. In contrast, during polymerization, the epoxy resins of the present invention shrink significantly less than the acrylate and methacrylate resin of the prior art. The present invention provides a system for curing epoxy resins in an acceptable time frame and to sufficient depth using visible light source equipment already available in the dental office.

The unique dental materials of the present invention may be filled or unfilled and include dental materials such as direct esthetic restorative materials (e.g., anterior and posterior restoratives), protheses, adhesives and primers for oral hard tissues, sealants, veneers, cavity liners, orthodontic bracket adhesives for use with any type of bracket (such as metal, plastic and ceramic), crown and bridge cements, artificial crowns, artificial teeth, dentures, and the like. These dental materials are used in the mouth and are disposed adjacent to natural teeth. The phrase "disposed adjacent to" as used herein will refer to the placing of a dental material in temporary or permanent bonded (e.g., adhesive) or touching (e.g., occlusal or proximal) contact with a natural tooth. The term "composite" as used herein will refer to a filled dental material. The term "restorative" as used herein will refer to a composite which is polymerized after it is disposed adjacent to a tooth. The term "prosthesis" as used herein will refer to a composite which is shaped and polymerized for its final use (e.g., as crown, bridge, veneer, inlay, onlay or the like) before it is disposed adjacent to a tooth. The term "sealant" as used herein will refer to a lightly filled composite or to an unfilled dental material which is cured after it is disposed adjacent to a tooth. "Polymerizable," as used herein, refers to curing or hardening the dental material, e.g., by free-radical, ionic or mixed reaction mechanisms.

Polymerization of the spiroorthocarbonate and epoxy/polyol mixture is initiated by adding suitable amounts of the photoinitiator and the optional sensitizer to the mixture and activating the initiator by exposure to a suitable light source. As one example, a photoinitiator comprising (4-octyloxyphenyl)phenyl-iodonium hexafluoroantimonate dissolved in methanol is added to the reaction mixture at a concentration level of 2 mole percent, and a photosensitizer comprising 2-chlorothioxanthen-9-one dissolved in methylene chloride is added to the reaction mixture at a concentration level of 0.2 mole percent. The reactants are then mixed by a suitable mixer to form a homogenized mixture which is then subjected to high vacuum to remove entrapped air and the majority of the volatile methanol and methylene chloride solvents introduced with the photoinitiator and photosensitizer. Removal of the volatile solvents is necessary to prevent shrinkage of the polymers during polymerization as a result of loss of the low molecular weight solvents.

Following application of the high vacuum, the reaction mixture is light activated by exposure to a light source such as a 275-watt high-intensity broad spectrum sun lamp. As previously mentioned, it is desirable in some applications to use a photoinitiator which will cause the polymerization to occur upon exposure to visible light.

The copolymer compositions of the present invention have utility as composites and in other applications. Notably, the lack of volume contraction and, in some instances, a slight expansion during polymerization make the copolymer compositions particularly useful in dental applications, SUCt1 as for dental fillings, precision castings, and strain-free composite matrix resins.

Filler particles can optionally be blended with the alicyclic spiroorthocarbonate and multifunctional copolymer composition to form a composite resin matrix for dental applications. The filler particles can be made of any suitable material but typically are inorganic in nature. Among the properties to be considered in selecting a filler are desired filler volume level, particle size, particle size distribution, index of refraction, radiopacity and hardness. Silicone dioxide is one example of a suitable filler, the filler particles can be produced by grinding or milling a material such as quartz or glass to an acceptable size, such as from 0.02 bm to 100 Um. A range of particles sizes is typically used to increase the amount of loading of filler material in the resin matrix. The amount of filler which can be added to the copolymer composition is dependent upon the total surface area of the filler particles. If colloidal size particles in the range of 0.02 to 0.04 Am are used, addition of a little as 5% by weight of the particles will be sufficient to modify the viscosity of the copolymer. Desirably, the filler can be present in an amount of between 20% and 80% by weight.

In order to increase the strength of the composite, a coupling agent can be used to increase the bonding strength of the copolymer to the filler particles. This enhanced bonding can improve the physical and mechanical properties of the composite and can provide hydrolytic stability by preventing water from penetrating along the interface between the copolymer and the filler.

A coupling agent should be chosen which is compatible with the copolymer and filler and will not significantly contribute to shrinkage of the composite during polymerization. Organosilanes are generally suitable coupling agents and commercially available 3-glycidoxypropyltrimethoxysilane is a preferred coupling agent when silicone dioxide is used as the filler material.

The photopolymerizable compositions of the invention are sensitive throughout the visible spectral region, and photocure rapidly, without the use of heat, to polymers having desirable properties. For purposes of the present invention, visible light is defined as light having a wavelength of between about 400 and 700 nanometers. The photopolymerization of the compositions of the invention occurs on exposure of the compositions to any source of radiation emitting actinic radiation at a wavelength within the visible spectral region. Exposures may be from less than about 1 second to 10 minutes or more, depending upon the amounts and particular components of the compositions utilized and depending upon the radiation source and distance from the source and the thickness of the composition to be cured. The compositions of the invention are one-part, stable compositions having very good shelf life and good thermal stability.

In certain applications, the use of a filler may be appropriate. The choice of filler affects important properties of the composite such as its appearance, radiopacity and physical and mechanical properties. Appearance is affected in part by adjustment of the amounts and relative refractive indices of the ingredients of the composite, thereby allowing alteration of the translucence, opacity or pearlescence of the composite. Epoxy resin compositions of the invention, either alone or in admixture with diluent monomer, can be prepared with refractive indices which approach or approximate the refractive indices of fillers such as quartz (refractive index 1.55), submicron silica (1.46), and 5.5:1 mole ratio $SiO_2:ZrO_2$ non-vitreous microparticles (1.54). In this way the appearance of the dental material can, if desired, be made to closely approximate the appearance of natural dentition.

Radiopacity is a measurement of the ability of the composite to be detected by x-ray examination. Frequently a radiopaque composite will be desirable, for instance, to enable the dentist to determine whether or not a filling remains sound. Under other circumstances a non-radiopaque composite may be desirable.

The amount of filler which is incorporated into the composite (referred to herein as the "loading level" and expressed as a weight percent based on the total weight of the dental material) will vary depending on the type of filler, the epoxy resin and other components of the composition, and the end use of the composite.

For some dental materials (e.g., sealants), the epoxy resin compositions of the invention can be lightly filled (e.g., having a loading level of less than about 40 weight percent) or unfilled. Preferably the viscosity of the dental material is sufficiently low to allow its penetration into pits and fissures of occlusal tooth surfaces as well as into etched areas of enamel, thereby aiding in the retention of the dental material. In applications where high strength or durability are desired (e.g., anterior or posterior restoratives, prostheses, crown and bridge cements, artificial crowns, artificial teeth and dentures) the loading level can be as high as about 95 weight percent. For most dental restorative and prosthetic applications a loading level of between about 70 and 90 weight percent is generally preferred.

Fillers may be selected from one or more of any material suitable for incorporation in compositions used for medical applications, such as fillers currently used in dental restorative compositions and the like. The filler is finely divided and preferably has a maximum particle diameter less than about 50 micrometers and an average particle diameter less than about 10 micrometers. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler should in any event be non-toxic and suitable for use in the mouth. The filler can be radiopaque, radiolucent or non-radiopaque.

Examples of suitable inorganic fillers are naturally-occurring or synthetic materials such as quartz, nitrides (e.g., silicon nitride), glasses derived from, for example, Ce, Sb, Sn, Zr, Sr, Ba and Al, colloidal silica, feldspar, borosilicate glass, kaolin, talc, titania, and zinc glass; low Mohs hardness fillers such as those described in U.S. Pat. No. 4,695,251; and submicron silica particles (e.g., pyrogenic silicas such as the "Aerosil" Series "OX 50," "130," "150" and "200" silicas sold by Degussa dn "Cab-O-Sil M5" silica sold by Cabot Corp.). Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169. Metallic fillers may also be incorporated, such as particulate metal filler made from a pure metal such as those of Groups IVA, VA, VIA, VIIA, VIII, IB, or IIB, aluminum, indium, and thallium of Group IIIB, and tin and lead of Group IVB, or alloys thereof. Conventional dental amalgam alloy powders, typically mixtures of silver, tin, copper, and zinc, may also optionally be incorporated. The particulate metallic filler preferably has an average particle size of about 1 micron to about 100 microns, more preferably 1 micron to about 50 microns. Mixtures of these fillers are also contemplated, as well as combination fillers made from organic and inorganic materials. Fluoroaluminosilicate glass fillers, either untreated or silanol treated, are particularly preferred. These glasses have the added benefit of releasing fluoride at the site of dental work when placed in the oral environment.

Optionally, the surface of the filler particles may be treated with a surface treatment such as a coupling agent in order to enhance the bond between the filler and the polymerizable resin. The coupling agent may be functionalized with reactive curing groups, such as acrylates, methacrylates, epoxies, and the like. Examples of coupling agents include gamma-methacryloxypropyltrimethoxysilane, gamma-mercaptopropyltriethoxysilane, gamma-aminopropyl-trimethoxysilane, beta-(3,4-epoxycyclohexyl)ethyl-trimethoxysilane, gamma-glycidoxypropyltri-methoxysilane, and the like.

The dental materials of the present invention can also contain suitable adjuvants such as accelerators, inhibitors, absorbers, stabilizers, pigments, dyes, viscosity modifiers, surface tension depressants and wetting aids, antioxidants, and other ingredients well known to those skilled in the art. For example, ethyldimethylaminobenzoate in amounts up to 1% by weight may be used as a reaction promoter.

The amounts and types of each ingredient in the dental material should be adjusted to provide the desired physical and handling properties before and after cure. For example, the cure rate, cure stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on experience with dental materials of the prior art.

When the dental material is applied to a tooth, the tooth can optionally be pre-treated with a primer such as dentin or enamel adhesive by methods known to those skilled in the art.

The following examples are given to illustrate, but not limit, the scope of this invention. Unless otherwise indicated, all parts and percentages are by weight, and all molecular weights are weight average molecular weight.

EXAMPLE 1

3,9-Diethyl-3,9-dihydroxymethyl-1,5,7,11-tetraoxaspiro[5.5]undecane

The title compound was prepared for use as an intermediate in the synthesis of spiroorthocarbonates of the present invention.

A 1000 mL 3-neck, round-bottom flask, equipped with a Dean-Stark trap, a reflux condenser, a thermometer, and a magnetic stirrer bar was charged with trimethylolpropane (65.1 g, 99%, 0.48 mol) and toluene (600 mL) under $N_2$. The mixture was heated to azeotropically remove moisture. Reflux continued for 1 h and 2×20 mL of azeoptropical mixture were collected in the Dean-Stark trap. Then solution was then allowed to cool to room temperature.

Tetraethylorthocarbonate (46.7 g, 98.7%, 0.24 mol) and anhydrous p-toluenesulfonic acid (0.3 g) were added, and the whole mixture was heated to reflux to azeotropically remove ethanol formed during the reaction. Azeotropic mixture was continually collected in the Dean-Stark trap until the pot temperature reached 110° C. A total of 203 mL of azeotropic mixture was obtained, which was shaken with salty water. After the aqueous layer was removed, the volume of organic layer (toluene) was measured to be 151 mL. So the amount of ethanol was 203−151=52 mL (55.2 in theory). After collecting azeotropic mixture, the reaction mixture was refluxed for another 1 h and then allowed to cool to room temperature TLC (Hexanes:EtOAc=1:3) showed that the starting triol almost disappeared and that a new spot was present which was due to the formation of SOCcompound. The reaction mixture was neutralized by adding triethylamine (~3 mL, pH~8) and allowed to stand under $N_2$ overnight.

A solid crude product separated upon standing overnight and was filtered to remove mother liquid. The crude product was purified by recrystallization from ether. It was dissolved in ~1100 mL of ether under reflux, and the resulting solution was cooled to room temperature, then kept in a refrigerator to crystallize. The crystals formed were collected by filtration, washed with ether (3×15 mL), and dried invacuo, giving 21.1 g of white crystal as 1st crop product, m.p. (DSC): 94.9° C. The filtrate was concentrated using a rotary evaporator to obtain a white solid which was recrystallized from ether again to afford 12.2 g of white crystals as 2nd crop product, m.p. (DSC): 94.9° C. The total yield of 1st and 2nd crops was 33.3 g, 50.2%; $^1$H NMR (CDCl$_3$, 300 Mhz) δ0.82 (t, 6H), 1.32 (q, 4H), 2.47 (s, 2H), 3.65–3.76 (m, 8H); $^{13}$C NMR (CDCl$_3$, 75 MHz) δ7.11, 23.03, 36.59, 61.74, 66.76, 67.25, 114.68. Anal. Calcd. for $C_{13}H_{24}O_6$; C, 56.51; H, 8.75. Found: C, 56.68; H, 9.07.

EXAMPLE 2

3,9-Dihydroxymethyl-3,9-dimethyl-1,5,7,11-tetraoxaspiro[5.5]undecane

The title compound was prepared for use as an intermediate in the synthesis of spiroorthocarbonates of the present invention.

A 500 mL 3-neck, round-bottom flask, equipped with a Dean-Stark trap, a reflux condenser, a thermometer, and a magnetic stirrer bar was charged with 1,1,1-tris(hydroxymethyl)ethane (29.1 g, 99%, 0.24 mol) and toluene (300 mL) under $N_2$. The mixture was heated to reflux to azeotropically remove moisture. Reflux was continued for 1.5 h. 2×20 mL of azeotropic mixture were collected in the Dean-Stark trap, and 75 mL of toluene were added in order to dissolve the triol completely. Then the mixture was allowed to cool to room temperature.

Tetraethylorthocarbonate (23.6 g, 98.4%, 0.12 mol), anhydrous p-toluenesulfonic acid (0.2 g), and 50 mL of toluene were added. The whole mixture was heated to reflux to azeotropically remove ethanol formed during the reaction. A heterogeneous system was observed throughout the reaction. 101.5 mL of azeotropic mixture were continually collected in the Dean-Stark trap which was shaken with salty water. After the aqueous layer was removed, the volume of the organic layer was measured to be 71.4 mL. So the amount of ethanol was 101.5−71.4=30.1 mL (28.1 in theory). After azeotropic removal of ethanol, 100 mL of o-xylene were added. The mixture was refluxed for another 2 h, and toluene was collected in the Dean-Stark trap during the reflux. The reaction mixture was allowed to cool to room temperature. TLC (Hexanes:EtOAc=2:3) revealed the disappearance of starting material and a new spot. Then the reaction mixture was neutralized by adding a mL of triethylamine (pH~8) and stood under $N_2$ overnight.

The solid in the flask was filtered and washed with toluene. This wet solid weighed 49 g as crude product which was purified by recrystallization from acetone. The crude product was dissolved in 650 mL of acetone under reflux. The solution was cooled to room temperature, then concentrated to ~450 mL, and kept in the refrigerator overnight to crystallize. The crystals were collected by filtration, washed with acetone (3×20 mL), and dried in vacuo, affording 18.5 g of white crystals as product (62.1% of theory). m.p. (DSC): 153.4° C. $^1$H NMR (CDCl$_3$, 300 Mhz) δ0.76 (s, 6H), 3.33 (d, 4H), 3.49–3.72 (m, 8H), 4.71 (t, 2H); $^{13}$C NMR (CDCl$_3$, 75 MHz) δ17.12, 33.80, 63.16, 67.38, 67.63, 113.89. Anal. Calcd. for $C_{11}H_{20}O_6$; C, 53.21; H, 8.12. Found: C, 53.32; H, 8.19.

EXAMPLE 3

3,9-Dihydroxymethyl-3,9-diphenyl-1,5,7,11-tetraoxaspiro[5.5]undecane α,α,α-Tris(hydroxymethyl)toluene The title compounds were prepared for use as intermediates in the synthesis of spiroorthocarbonates of the present invention.

This triol was prepared by the Cannizzaro reaction of phenylacetalaldehyde with paraformaldehyde. A 1000 mL 3-neck flask, equipped with a reflux condenser, a thermometer, and a magnetic stir bar, was charged with phenylacetalaldehyde (119.4 g, 90%, 0.9 mol), paraformaldehyde (176.8, 95%, 5.6 mol), Ca(OH)$_2$ (52 g, 0.7 mol), and THF (600 mL) under $N_2$. The suspension was heated to 60°–65° C. with stirring and was continuously stirred at this temperature for 2 days. After cooling to room temperature, the reaction mixture was filtered through ~2 cm thick of Celite. The filtrate was concentrated under reduced pressure using a rotary evaporator, and the residue was a highly viscous oil as crude product (248.7 g).

This crude product was purified by distillation. A distillation flask containing crude product was connected to a distillation apparatus and was evacuated without heating to remove low boiling point solvent and byproducts. The flask was then heated and the product was distilled at 167°–185° C./1–1.5 mmHg as a highly viscous liquid, which crystallized upon standing at room temperature. There was a layer of viscous oil at the top of the crystals. TLC (Hexanes:EtOAc=2:3) and IR characterizations showed that it could be an intermediate (a less polar spot and a C=O absorption) which was not converted to the product. The oil was decanted, and the crystals were washed with 200 mL of ether and filtered to remove mother liquid. The crystals were washed with ether again (3×50 mL) and dried in vacuo to afford 72 g of white crystals as product, yield: 44% of theory. m.p. (DSC): 88.7° C. $^1$H NMR (DMSO, 300 MHz) δ3.71 (d, 6H), 4.41 (t, 3H), 7.14 (t, 1H), 7.25 (d, 2H), 6.41 (d, 2H).

3,9-Dihydroxymethyl-3,9-diphenyl-1,5,7,11-textraoxaspiro[5.5]undecane via TEOC method A 500 mL 3-neck, round-bottom flask, equipped with a Dean-Stark trap and a reflux condenser, a thermometer, and a magnetic stir bar, was charged with α,α,α-trismethyloltoluene (43.7 g, 0.24 mol) and toluene (300 mL) under $N_2$. The mixture was heated to reflux to azeotropically remove moisture. 2×20 mL of azeotropic mixture were collected in the Dean-Stark trap within 30 min, and the mixture was allowed to cool to room temperature. Tetraethylorthocarbonate (23.8 g, 97%, 0.12 mol) and anhydrous p-toluenesulfonic acid (0.2 g) were added followed by adding another 70 mL of toluene in order to obtain a homogeneous system. The whole mixture was heated to reflux to azeotropically remove ethanol formed during the reaction. 140 mL of azeotropic mixture was continuously collected, which was shaken with salty water. After aqueous layer was removed, the volume of organic layer (toluene) was measured to be 128 mL. The amount of ethanol was 140−128=121 mL (28 mL in theory). This indicated that the reaction was incomplete.

The reaction mixture was allowed to cool, and o-xylene (200 ml) was added to replace toluene. Another 0.1 g of p-toluenesulfonic acid was added, and the mixture was heated to reflux to continuously collect azeotrope mixture in the Dean-Stark trap. When 230 mL of azeotropic mixture were collected, TLC (Hexanes:EtOAc=2:3) revealed the disappearance of the starting triol and a new spot which was due to the formation of SOC. By shaking the azeotropic mixture with salty water, another 12–13 mL of ethanol were obtained. The total volume of ethanol was 12+13=25 mL (28 mL in theory). Then the reaction mixture was cooled to room temperature and neutralized by adding triethylamine (~2 mL, pH ~8). During cooling, crystals came out of the solution. o-xylene was removed under reduced pressure using a rotary evaporator to afford white solid as crude product.

The crude product was purified by recrystallization from acetone. The crude product was first dissolved in acetone (~400 mL) under reflux, then the solution was cooled to room temperature and concentrated to a volume of ~150 mL, and kept in the refrigerator to crystallize. The crystals formed were collected by filtration, washed with acetone (3×10 mL), and dried in vacuo to afford 20.3 g (45% of theory) of white powdery crystals. m.p. (DSC): 173.3° C. $^1$H NMR (DMSO, 300 MHz) $\delta$3.72 (d, 4H), 4.02–4.27 (m, 8H), 4.84 (t, 2H), 7.30 (m, 10H); $^{13}$C NMR (DMSO, 75 MHz) $\delta$40.60, 63.07, 65.92, 66.27, 113.90, 126.54, 128.16, 140.82. Anal. Calcd. for $C_{21}H_{24}O_6$; C, 67.73; H, 6.50. Found: C, 67.65; H, 6.73.

3,9-Dihydroxymethyl-3,9-diphenyl-1,5,7,11-textraoxaspiro[5.5]undecane via TIN method A 500 mL 3-neck, round-bottom flask, equipped with a Dean-Stark trap and a reflux condenser, a thermometer, and a magnetic stir bar, was charged with $\alpha,\alpha,\alpha$-trismethyloltoluene (27.4 g, 0.15 mol), bis(tri-n-butyltin) oxide (89.4 g, 0.15 mol), and toluene (200 mL) under $N_2$. The mixture was slowly heated to reflux under $N_2$ using a Dean-Stark trap to collect water formed during the reaction. Azeotropic removal of water was continued overnight. 2.8 mL of water were collected (2.7 mL in theory). The reaction mixture was cooled to room temperature, then to 0° C. Carbon disulfide (9 mL, 0.15 mol) was added dropwise to the reaction mixture through an addition funnel at 0° C. After the addition of carbon disulfide was complete, the reaction mixture was allowed to warm to room temperature followed by slowly heating to reflux. Reflux continued overnight. The reaction mixture was cooled to room temperature. Solid precipitated from the solution, the upper clear solution was decanted and concentrated using a rotary evaporator. The liquid containing Tin-S byproduct in the residue was decanted. The solids were combined which was dissolve in $CH_2Cl_2$ (30 mL), and the solution was taken up in 30 mL of acetone. The white solid formed was filtered, giving 45 g of wet crude product, which purified by recrystallization from acetone. The white solid was dissolved in ~250 mL of acetone under reflux, and the solution was cooled to room temperature, the concentrated to a volume of 150 mL. This solution was kept in the refrigerator overnight to recrystallize. The crystals formed were collected by filtration, washed with acetone (3×10 mL), and dried in vacuo, affording 15.0 g of white powdery crystals as product (53.8% of theory). m.p. (DSC): 175° C.

EXAMPLE 4

3,9-Diacetoxymethyl-3,9-diethyl-1,5,7,11-tetraoxaspiro[5.5]undecane (DAMDE)

This SOC compound was prepared by reacting the parent SOC, 3,9-diethyl-3,9-dihydroxymethyl-1,5,7,11-tetraoxaspiro[5.5]undecane as prepared in Example 1 (DEDHM-SOC), with acetic anhydride in the presence of pyridine. A 250 mL one-neck flask was charged with DEDHM-SOC (5.0 g, 0.018 mol) and pyridine (25 mL, 0.27 mol) was added. The mixture was stirred at room temperature for 4 h. TLC revealed the disappearance of starting material and a new product spot (less polar). The mixture was then concentrated under reduced pressure using a rotary evaporator to a viscous oil which crystallized upon standing in the refrigerator overnight. These crystals were further purified by recrystallization from cyclohexane. 6.2 g of the crude product was dissolved in 30 mL of cyclohexane under reflux, and the solution was cooled to room temperature to crystallize. The crystals were collected by filtration, washed with cyclohexane (3×10 mL), and dried in vacuo. 5.3 g of white crystals were obtained as product (81% of theory). m.p. (DSC): 71.4° C.; $^1$H NMR (CDCl$_3$, 300 Mhz) $\delta$0.79 (t, 6H), 1.33 (q, 4H), 2.02 (s, 6H), 3.71 (m, 4H), 3.71 (m, 4H),(m, 4H), 4.14 (s, 4H); $^{13}$C NMR (CDCl$_3$, 75 MHz) $\delta$7.04, 20.70, 23.29, 35.27, 63.34, 66.66, 67.05, 114.60, 170.68. Anal. calcd. for $C_{17}H_{28}O_8$; C, 56.65; H, 7.83. Found: C, 56.89; H, 7.94.

EXAMPLE 5

3,9-Diacetoxymethyl-3,9-dimethyl-1,5,7,11-tetraoxaspiro[5.5]undecane (DAMDM)

A 100 mL one-neck round-bottom flask was charged with 3,9-dihydroxymethyl-3,9-dimethyl-1,5,7,11-tetraoxaspiro [5.5]undecane prepared as in Example 2 (DHMDM-SOC, 4.6 g, 0.0185 mol) and pyridine (25 mL) under $N_2$. After DHMDM-SOC was dissolved, acetic anhydride (26.2 mL, 0.28 mole) was added. The mixture was stirred at room temperature for 4 h. TLC (1:3 Hexanes:EtOAc) revealed the disappearance of DHMDM-SOC and a new product spot (Rf~0.6). Pyridine and unreacted acetic anhydride were removed under reduced pressure using rotary evaporator. The residue was off-white solid as crude product. It was purified by recrystallization from cyclohexane. The solid was dissolved in ~300 mL of cyclohexane, and the solution was cooled to room temperature, kept in refrigerator overnight to crystallize. The crystals were collected by filtration, washed with cyclohexane (3×20 mL), and dried in vacuo, giving 5.7 g of white crystals as product (93.4 % of theory). m.p. (DSC): 137.4° C.; $^1$H NMR (CDCl$_3$, 75 Mhz) $\delta$0.87 (s, 6H), 2.05 (s, 6H); 3.65–3.80 (m, 8H), 4.12 (s, 4H); $^{13}$C NMR (CDCl$_3$, 75 MHz) $\delta$1711, 20.73, 32.88, 66.17, 67.87, 68.26, 114,20, 170.78. Anal. calcd. for $C_{15}H_{24}O_8$; C, 54.21; H, 7.28. Found: C, 54.31; H, 7.48.

EXAMPLE 6

3,9-Diethyl-3,9-dipropionyloxymethyl-1,5,7,11-tetraoxaspiro[5.5]undecane (DEDPM)

This SOC compound was prepared by reacting the parent SOC, 3,9-diethyl-3,9-dihydroxymethyl-1,5,7,11- tetraoxaspiro[5.5]undecane prepared as in Example 1 (DEDHM-SOC), with propionic anhydride in the presence of pyridine. A 100 mL one-neck flask was charged with DEDHM-SOC (5.0 g, 0.018 mol) and pyridine (25 mL) under $N_2$. After DEDHM-SOC was dissolved in pyridine, propionic anhydride (34.8 mL, 0.27 mol) was added. The mixture was stirred at room temperature for 4 h. TLC revealed the disappearance of staring material and a new product spot (less polar). Pyridine and unreacted propionic anhydride were removed by distillation under reduced pressure. The pot temperature should not exceed 40° C. during the distillation. The residual viscous liquid was dried in vacuo for 3 h, and it crystallized upon standing at room temperature. The crystals were purified by recrystallization from cyclohexane. 18 mL of cyclohexane were used to dissolve the crystals under reflux. The solution was cooled to room temperature, then kept in a refrigerator overnight to crystallize. The crystals formed were collected by filtration, washed with cyclohexane (3×5 mL), and dried in vacuo. 5.0 g of white crystals were obtained as product (71.1% of theory). m.p. (DSC): 68.1° C.; $^1$H NMR (CDCl$_3$, 300 MHz) $\delta$0.81 (t, 6H), 1.11 (t, 6H); 1.35 (q, 4H), 2.32 (q, 4H), 3.73–3.81 (m, 8H), 4.15 (s, 4H); $^{13}$C NMR (CDCl$_3$, 75 MHz) $\delta$7.10, 9.05, 23,38, 27.44, 35.42, 63.20, 66.74, 67.10, 114.66, 174.06. Anal. calcd. for $C_{19}H_{32}O_8$; C, 58.75; H, 8.30. Found: C, 58.86; H, 8.53.

EXAMPLE 7

3,9-Diacetoxymethyl-3,9-diphenyl-1,5,7,11-tetraoxaspiro[5.5]undecane (DAMDP)

A 100 mL one-neck round-bottom flask was charged with 3,9-dihydroxymethyl-3,9-diphenyl-1,5,7,11-tetraoxaspiro[5.5]undecanes prepared in Example 3 (DHMDP-SOC, 3.8 g, 0.01 mol) and pyridine (23 mL) under $N_2$. DPDHM-SOC was not totally dissolved in pyridine. Acetic anhydride (14 mL, 0.15 mL) was added, and a clear solution was formed. The mixture was stirred at room temperature. 3 h later, TLC (2:3 Hexanes:EtOAc) revealed that DPDHM-SOC disappeared and two new spots were observed. One is due to the formation of the product, the other was from byproduct (pyridine salt). The reaction mixture was concentrated under reduced pressure using rotary evaporator, and the residue was a viscous liquid which was purified by column chromatography. The reaction mixture was absorbed onto a small amount of Silica gel (~10 g) and the loaded onto a column (3.0 cm 2D) packed with Silica gel (~100 g). The column was eluted with 2:1–1:1 Hexanes:EtOAc. After removing solvent, 4.0 g of white viscous liquid was obtained which was further recrystallized from cyclohexane. The solid was dissolved in 30 mL of cyclohexane under reflux. A sticky solid was found upon cooling the solution to room temperature, and it was collected by filtration, dried in vacuo, and weighed 3.8 g as product (82.6% of theory). m.p. (DSC): 31.0° C. (broad peak); $^1$H NMR (CDCl$_3$, 300 Mhz) $\delta$1.95 (s, 6H), 4.21 (s,4H), 4.29 (d, 2H), 4.46 (d,2H), 4.59 (s, 4H), 7.20–7.39 (m, 10H); $^{13}$C NMR (CDCl$_3$, 75 MHz) $\delta$20.69, 39.17, 65.30, 66.63, 67.09, 11425, 125.73, 128.68, 127.48, 138.41, 170.51. Anal. Calcd. for $C_{25}H_{28}O_8$; C, 65.78; H, 6.18. Found: C, 65.85; H, 6.22.

EXAMPLE 8

3,9-Dibenzyloxymethyl-3,9-dimethyl-1,5,7,11-tetraoxaspiro[5.5]undecane (DBOMDM) cis- and trans-2-Isopropyl-5-hydroxymethyl-5-methyl-1,3-dioxane A 500 mL 3-neck, round-bottom flask, fitted with a Dean-Stark trap and a reflux condenser, a thermometer, and a magnetic stir bar, was charged with tris-1,1,1-hydroxymethylethane (42.5 g, 0.35 mol), isobutyraldehyde (25.2 g, 0.35 mol), petroleum ether (35°–60° C, 250 mL), and p-toluenesulfonic acid monohydrate (4.0 g). The mixture was warmed to reflux to collect water formed during the reaction. 4 hours later, ~7 mL of water was collected in the Dean-Stark trap (6.3 mL in theory). Then the mixture was cooled to room temperature. NaOAc (3.5 g) was added, and stirring continued for 30 minutes. The mixture was taken up in 500 mL of ether and washed with two 250 mL portions of water. The ether solution was dried over MgSO$_4$. After removing MgSO$_4$ by filtration, the ether solution was concentrated using a rotary evaporator to afford 64.4 mL colorless liquid as crude product. Purification by distillation yielded 45.9 g (75% of theory) of product, b.p. 116°–139° C. (0.5–0.75 mmHg). IR (neat): 3420, 2955, 2845, 1457, 1393, 1369, 1302, 1272, 1246, 1208, 1186, 1145, 1102, 1040, 944, 950, 920, 905 cm$^{-1}$; $^1$H NMR (CDCl$_3$, 300 Mhz) $\delta$0.69 (s, 3H), 0.90 (d, 6H), 1.77 (m, 1H), 2.36 (s, 1H), 3.38 (d, 2H), 3.73 (s, 2H), 3.87 (d, 2H), 4.17 (d, 1H); $^{13}$C NMR (CDCl$_3$, 75 MHz) $\delta$16.80, 16.86, 32.45, 34.79, 65.69, 72.94, 105.77.

2-Isopropyl-5-benzyloxymethyl-5-methyl-1,3-dioxane

A 2 L 3-neck, round-bottom flask fitted with $N_2$-inlet, addition funnel, a thermometer, and magnetic stir bar, was flamed-dried, flushed with $N_2$ and charged with sodium hydride (10.0 g, 0.25 mol, 60% dispersion in oil), n-tetrabutylammonium iodide (27 g, 0.07 mol), and dry THF (450 ml, adding through a syringe). The mixture was stirred under $N_2$ and cooled to 0° C. in an ice-bath. A solution of 2-isopropyl-5-hydroxymethyl-5-methyl-1,3-dioxane (cis and trans mixture, 45 g, 0.25 mol) in 225 mL of dry THF was added portionwise at 0° C. The mixture was stirred at room temperature for 1 h, then benzyl bromide (82.6 g, 0.48 mol) was added dropwise at 0° C. and the whole was left overnight at room temperature. The reaction was quenched by adding 25 mL of methanol. The solid was filtered off, and the filtrate was concentrated using a rotary evaporator. The residue was poured into ~300 ml of water and was extracted with ether (3×250 ml). The ether solution was dried over MgSO$_4$ and concentrated to an oil which was applied to a column of Silica gel and eluted with 20:1 Hexanes:EtOAc. The tubes containing the product were combined and concentrated using rotary evaporator to give 22.7 g of oil as product. The tubes containing both starting material (benzyl bromide) and product were combined and concentrated to give 54.2 g of mixture which was further distilled to give 28.5 g of oil as product, b.p. 118°–120° C./0.55–0.6 mmHg). IR (neat): 3050, 3020, 2950, 2840, 1447, 1390, 1357, 1300, 1244, 1220, 1203, 1182, 1169, 1158, 1148, 1100, 1032, 1024, 996, 950, 920, 905, 730, 690 cm$^{-1}$; $^1$H NMR (CDCl$_3$, 300 Mhz) $\delta$0.77 (s), 0.94 (d), 0.97(d), 1.24 (s), 1.81 (m), 3.12 (s), 3.38 (d), 3.62 (s), 3.72 (d), 3.94(d), 4.20 (d), 4.67(s), 4.58(s), 7.28–7.36 (m); $^{13}$C NMR (CDCl$_3$, 75 MHz) $\delta$16.81, 16.91, 17.50, 19.15, 32.49, 34.50, 34.75, 72.64, 73.06, 73.28, 73.72, 74.28, 105.64, 105.75, 127.28, 127.33, 127.55, 128.19, 128.33, 138.81.

2-Benzyloxymethyl-2-methyl-1,3-propanediol

A 2 L 3-neck, round-bottom flask, equipped with a reflux condenser, a thermometer, and magnetic stir bar, was charged with 2-isopropyl-5-benzyloxymethyl-5-methyl-1,3-dioxane (48.5 g, 0.183 mol), IN HCI (330 mL), and methanol (600 mL). The mixture was heated to reflux for 3 h, then neutralized with 1N NaOH (~330 mL). The mixture was extracted with CH$_2$Cl$_2$ (600 mL), and the organic layer was separated. The aqueous layer was extracted with 250 mL of CH$_2$Cl$_2$. The combined organic layer was washed with brine (300 ML), and dried over MgSO$_4$. After removing MgSO$_4$, the solution was concentrated using a rotary evaporator under reduced pressure. The residual oily mixture was purified by column chromatography. It was applied to a column of Silica gel and eluted with 5:1 and 2:3 Hexanes:EtOAc to give 12.5 g of white crystals after removing solvent and drying in vacuo (33% of theory). m.p. (DSC): 54.5° C.; IR (neat): 3280, 2930, 2860, 2840, 1448, 1403, 1354, 1296, 1200, 1150, 1108, 1050, 1021, 990, 962, 892, 727, 688 cm$^{-1}$; $^1$H NMR (CDCl$_3$, 300 Mhz) δ0.84 (s, 3H), 2.92 (s, 2H), 3.45(s, 2H), 3.57 (d, 2H), 3.69 (d, 2H), 4.51 (s, 2H), 7.32 (m, 5H); $^{13}$C NMR (CDCl$_3$, 75 MHz) δ17.09, 40,77, 67.71, 73.56, 75.49, 127.47, 127.72, 128.43, 137.87.

3,9-Dibenzyloxymethyl-3,9-dimethyl-1,5,7.11-tetraoxaspiro[5.5]undecane

A 250 mL 3-neck, round-bottom flask, equipped with a Dean-Stark trap and a reflux condenser, a thermometer, and a magnetic stir bar, was charged with 2-benzyloxymethyl-1,3-propanediol (5.3 g, 0.025 mol) and toluene (100 mL) under N$_2$. The mixture was heated to reflux to azeotropically remove moisture. 24 mL of azeotropic mixture were collected in the Dean-Stark trap, then the solution was allowed to cool to room temperature. Tetraethylorthocarbonate (2.46 g, 98.4%, 0.0126 mol) and anhydrous p-toluenesulfonic acid (65 mg) were added, and the whole mixture was heated to reflux to azeotropically remove ethanol formed during the reaction. After 9.6 mL of azeotropic mixture was collected in the Dean-Stark trap, reflux continued for another 2 h. The azeotropic mixture was shake with salty water to give 6.6 mL of toluene. So the amount of ethanol was 9.6–6.6=3.0 mL (2.96 mL in theory). After the reaction mixture was cooled to room temperature, it was neutralized by adding 6 drops of triethylamine (pH ~8) and stood under N$_2$ overnight. Toluene was removed under reduced pressure using a rotary evaporator. The white solid residue was purified by recrystallization from ether. 5.4 g of white solid was dissolved in 30 mL of ether under reflux. The solution was cooled to room temperature, then kept in a refrigerator to crystallize. The crystals were collected by filtration, washed with ice-cold ether (3×10 mL), and drying in vacuo, giving 3.7 g of white crystals as product (68.5% of theory). m.p. (DSC): 91.1° C.; $^1$H NMR (CDCl$_3$, 300 Mhz) δ0.95 (s, 6H), 3.52 (d, 4H), 3.67–3.91 (m, 8H), 4.55 (s, 6H), 7.34 (m, 10H); $^{13}$C NMR (CDCl$_3$, 75 MHz) δ17.63, 33,89, 68.25, 68.70, 72.61, 73.34, 114.39, 127.36, 127.42, 128.26, 138.52. Anal. Calcd. for C$_{25}$H$_{32}$O$_8$; C, 70.07; H, 7.58. Found: C, 70.17; H, 7.83.

EXAMPLE 9

3,9-Diethyl-3,9-di(isopropylcarbamoyloxymethyl)-1,5,7,11-tetraoxaspiro[5.5]undecane (DEDPCM)

A 100 ml 3-neck round bottom flask, equipped with a reflux condenser, a thermometer and a magnetic stirrer bar was charged with 3,9-diethyl-3,9-dihydroxymethyl-1,5,7,11-tetraoxaspiro[5.5]undecane prepared as in Example 1 (20.7 g, 95.5%, 0.0749 mole) and toluene (550 ml) under N$_2$. The mixture was heated to 60° C. when the solution became clear. Then a small drop of dibutyltindilaurate was added followed by isopropylisocyanate (17.5 g, 98%, 0.2015 mole). The reaction mixture was heated to reflux for 30 minutes. TLC (ethyl acetate/hexane 2/1) showed the starting material (Rf.19) had disappeared and a clean new spot (Rf.43) had shown up. The mixture was then cooled down to room temperature and was stripped of toluene by means of rotary evaporator. IR of this resulting solid showed no —NCO but the strong —C=O and ether link. The solid was recrystallized in 600 ml of ethylether. The crystals were filtered and vacuum dried for 30 hours at room temperature. The 1st crop 26.9 g, 2nd crop 1 g, and 3rd crop 3.6 g, total 31.5 g were obtained with DSC purity/mp° C.:

DSC purity 97.50 mole %, mp 139.5° C.
DSC purity 96.32 mole %, mp 139.2° C.
DSC purity 98.94 mole %, mp 140.0° C.

(The 2nd crop was recrystallized again for >99 mole % purity samples.)

Total yield of the three crops was 90.8%.

EXAMPLE 10

3,9-Diethyl-3,9-di(4-tolyl-carbamoyloxymethyl)-1,5,7,11-tetraoxaspiro[5.5]undecane (DEDTCM)

A 500 mL 3-neck, round-bottom flask, equipped with a reflux condenser, a thermometer and a magnetic stirrer bar was charged with 3,9-diethyl-3,9-dihydroxymethyl-1,5,7,11-textraoxaspiro[5.5]undecane (8.5 g, 0.0308 mol) and toluene (210 mL) under N$_2$. The mixture was heated to 60° C. when the solution became clear. Then a small drop of dibutyltindilaurate was added followed by p-tolylisocyanate (12.4 g, 99.0%, 0.0924 mol). The reaction mixture was further heated to reflux for 30 min. TLC (ethyl acetate:hexane, 1:1) showed the starting material (Rf 14) had disappeared and a clean new spot (Rf 66) had shown up. The mixture was then cooled down to room temperature and became slightly cloudy. About 0.4 g of precipitate was filtered off and the filtrate was stripped of toluene by means of a rotary evaporator and further dried for 2 hr at 80° C. under vacuum. IR of the resulting beige solid showed very little —NCO but with strong —C=O, —NH and ether link. DSC showed two melting points. The solid was recrystallized in 1 L of ethylether. The white crystals were filtered and vacuum dried for 12 hr at room temperature. The 1st crop yielded 2.2 g, 2nd crop 9.5 g, and 3rd crop 0.3 g, total 12.0 g were obtained with DSC purity/ m.p.° C.:

DSC purity 98.79 mole % m.p. 171.8° C.
DSC purity 98.25 mole %, m.p. 171.4° C.
DSC purity 99.58 mole %, 170.0° C.

IR (KBr) showed no —NCO, strong —C=O and ether link. The total yield of the three crops was 72.1%.

EXAMPLE 11

3,9-Diethyl-3,9-di(n-propylsulfonyloxymethyl)-1,5,7,11-tetraoxaspiro[5.5]undecane (DEDPSM)

A 250 mL 3-neck, round-bottom flask, equipped with a reflux condenser, a thermometer and a magnetic stirrer bar was charged with 3,9-diethyl-3,9-dihydroxymethyl-1,5,7,11-tetraoxaspiro[5.5]undecane (10.2 g, 0.0364 mol) and pyridine (100 mL) under $N_2$. The clear solution was cooled to $-2°$ C. by using a salt ice bath, then n-propylsulfonyl chloride (9.3 mL, 97%, 0.0801 mol) was added. Slight exotherm was observed. After 1 hr the mixture was allowed to warm up to room temperature. The reaction was followed by TLC. After 3.5 hr TLC (EtOAc:hexane, 2:1) showed that the starting material was almost gone and two new spots (Rf .8 and .55, respectively) had shown up. The reaction mixture was stirred overnight. This time the TLC showed only one spot (Rf .8). The mixture was then filtered and the filtrate was rinsed by toluene, was filtered away and precipitated again, was concentrated by rotary evaporating the solvents and was rediluted by toluene until the solution was clear. The solvents were then stripped and the residue was dried ($70°-80°$ C.) for 1 hr under vacuum. IR showed no —OH, very small carbonyl, strong 1375, 1175 $cm^{-1}$ and ether link. After vacuum drying 21.2 g of crude amberish syrup was obtained along with the salt about 8.2 g. The latter was soluble in water.

The syrup was run through column chromatography, using 120 g silica gel and a gradient mobile phase of ethyl acetate:hexane, 1.5:1 and 4:1, 500 mL and 600 mL respectively. The title compound rich eluants were decolorized by activated carbon, Norit A. After stripping the solvents and drying under vacuum at room temperature 14.1 g beige syrup (Rf .8) along with 1.8 g (with small impurities) were produced, total yield 93.0%. The products solidified upon sitting at room temperature, were recrystallized in 70 mL of ether and the crystals washed with another 50 mL. This gave 5.9 g of white solids. DSC (slow melting point °C.): purity 98.68 mole %, m.p. $58.7°$ C.; $^1H$ NMR ($CDCl_3$, 300 MHz): d 0.85–0.90 (t, 3H), 1.05–1.10 (t, 3H), 1.34–1.41 (q, 2H), 1.81–1.94 (m, 2H), 3.08–3.13 (m, 2H), 3.74–3.95 (m, 4H), 4.32–4.34 (q, 2H); $^{13}C$ NMR ($CDCL_{13}$, 75 MHz): d 6.77 12,82, 17.21, 22,89, 35.91, 51.57, 66.23, 66.74, 67.10, 114.16. Elemental analysis: C, 46.64; H, 7.66; S, 13.26. Theory: C, 46.7; H, 7.44; S, 13.12.

EXAMPLE 12

Polymeric compositions were prepared by mixing 20 wt % spiroorthocarbonates prepared as in the preceding examples with 80 wt % of an 80/20 wt % mixture of epoxy/polytetrahydrofuran (MW ca. 250) and 1 wt % of the photoinitiator OPIA and 0.5 wt % of the photosensitizer CQ. The resulting mixtures were then photopolymerized. Polymeric compositions from the following mixtures were prepared:

| Test sample | SOC | Epoxy/PTHF |
|---|---|---|
| 1 | DAMDE | UVR-6105/PTHF |
| 2 | DEDPM | UVR-6105/PTHF |
| 3 | DBDPM | ERL-4299/PTHF |
| 4 | DBOMDM | UVR-6105/PTHF |
| 5 | DAMDE | UVR-6105/PTHF |
| 6 | DAMDE | ERL-4206/PTHF |
| 7 | DAMDE | ERL-4299/PTHF |
| 8 | DEDPM | UVR-6105/PTHF |
| 9 | DEDPM | ERL-4206/PTHF |
| 10 | DEDPM | ERL-4299/PTHF |

Selected mixtures were also tested to evaluate the rate and extent of the polymerization of the mixtures during irradiation with visible light. The photopolymerization characteristics were determined using a Dupont differential scanning calorimeter (DSC) equipped with a Dupont differential photocalorimeter (DPC), containing a 200 watt mercury lamp which was filtered so as to emit light at a wavelength greater than 418 nm (Dupont Model 910 DSC with DPC 930 unit, TA Instruments USA, Inc., New Castle, Del.). A sample weighing 17 to 19 milligrams was placed in a DSC liquid sample pan and irradiated for 20 minutes at $30°$ C. The intensity of the light was about 32 microwatt/$cm^2$. The photopolymerization parameters measured for each example were: enthalpy of reaction ($\Delta H$), induction time, time to maximum exotherm, and percent conversion at maximum. The photopolymerizations were further characterized by generating conversion and rate plots and calculating rate constants (k). The test results are set forth in Table 1:

TABLE 1

| Sample No. | $\Delta H$photo (J/g) | Ind. time (sec) | Time to max. (sec)[a] | Photo Conv. at peak (%) | k (min$^{-1}$) |
|---|---|---|---|---|---|
| 1 | 256 | 17 | 25 | 11 | 3.2 |
| 6 | 587 | 15 | 19 | 18 | 7.0 |
| 7 | 168 | 15 | 23 | 10 | 0.9 |
| 2 | 346 | 16 | 24 | 17 | 9.9 |
| 9 | 559 | 18 | 22 | 19 | 8.9 |
| 10 | 209 | 15 | 22 | 12 | 2.5 |

[a]Induction time = time to reach 1% conversion during the photoreaction.
Note: All mixtures contained OPIA/CQ 1 wt %/0.5 wt %.

EXAMPLE 13

Polymeric compositions were prepared and tested to determine the effect that the spiroorthocarbonates have on the bulk polymerization shrinkage of the epoxy resins. The results are set forth in Table 2:

TABLE 2

| Resin Type | Resin wt % | SOC wt % | SOC Type | Shrinkage % | % Shrinkage Reduction |
|---|---|---|---|---|---|
| Epoxy[a] p-THF | 100 | 0 | None | 4.19 ± 0.12 | 0 |
| Epoxy[a] p-THF | 60 | 40 | SOC DEDPM | 3.08 ± 0.14 | 27 |
| Epoxy[a] p-THF | 60 | 40 | Soc DAMDE | 3.05 ± 0.18 | 27 |
| Epoxy[b] p-THF | 60 | 40 | SOC DEDPM | 1.91 ± 0.17 | 42 |

[a]80 wt % Epoxy (UVR 6105)/20 wt % Polyol (p-THF)
[b]80 wt % Epoxy (ERL 4290)/20 wt % Polyol (p-THF)
Note: All mixtures contained OPIA/CQ 1 wt%/0.5 wt %.

EXAMPLE 14

Further polymeric compositions of the present invention were prepared to determine the compatibility of the spiroorthocarbonates, epoxy resins and polyols with each other. The component mixtures are set forth in Table 3:

TABLE 3

Composition and Test Status of Spiroorthocarbonate/Epoxy/Polyol Mixtures

| Sample No. | Epoxy | wt % | Polyol | wt % | SOC | wt % | Initiator | wt %[a] | Sensitizer | wt %[a] | Promoter | wt %[a] | Tested (yes or no) | Status |
|---|---|---|---|---|---|---|---|---|---|---|---|---|---|---|
| 1 | ERL-4299 | 68 | TEG | 12 | DEDPSM | 20 | CD-1012 | 1.0 | CQ | 0.5 | — | — | Yes | OK |
| 2 | UVR-6105 | 76.5 | PEG-200 | 13.5 | DAMDE | 10 | OPIA | 1.0 | CQ | 0.5 | EDMAB | 0.2 | Yes | OK |
| 3 | ERL-4299 | 81 | TONE 301 | 9 | DEDPM | 10 | CD-1012 | 1.5 | CQ | 0.5 | EDMAB | 0.1 | Yes | OK |
| 4 | ERL-4206 | 60 | PEG-200 | 15 | DEDPSM | 25 | OPIA | 1.5 | CQ | 0.75 | — | — | Yes | OK |
| 5 | UVR-6105 | 72 | TEG | 8 | DEDPM | 20 | OPIA | 2.0 | CQ | 1.0 | — | — | Yes | OK |
| 6 | ERL-4299 | 60 | CHDM | 15 | DAMDE | 25 | CD-1012 | 1.o | CQ | 0.5 | — | — | Yes | OK |
| 7 | UVR-6105 | 72 | TONE 301 | 18 | DEDTCM | 10 | OPIA | 1.0 | CQ | 0.5 | EDMAB | 0.2 | Yes | OK |
| 8 | ERL-4299 | 81 | CHDM | 9 | DEDPSM | 10 | OPIA | 1.5 | CQ | 0.5 | EDMAB | 0.1 | Yes | OK |
| 9 | ERL-4299 | 76.5 | TONE 201 | 8.5 | DAMDE | 15 | OPIA | 1.5 | CQ | 0.75 | — | — | Yes | OK |
| 10 | UVRL-6105 | 68 | TONE 201 | 12 | DEDPSM | 20 | OPIA | 1.0 | CTX | 0.5 | — | — | Yes | OK |
| 11 | ERL-4206 | 76.5 | TONE 301 | 13.5 | DAMDE | 10 | CD-1012 | 1.5 | CQ | 0.5 | — | — | Yes | OK |
| 12 | ERL-4299 | 72 | CHDM | 18 | DEDPM | 10 | OPIA | 1.5 | CTX | 0.5 | — | — | Yes | OK |
| 13 | ERL-4206 | 72 | TONE 201 | 8 | DEDPM | 20 | CD-1012 | 1.o | CQ | 0.5 | — | — | Yes | OK |
| 14 | ERL-4299 | 60 | PEG-200 | 15 | DAMDE | 25 | OPIA | 1.0 | CTX | 1 | EDMAB | 0.1 | Yes | OK |
| 15 | ERL-4299 | 81 | PEG-200 | 9 | DEDPSM | 10 | CD-1012 | 2.0 | CQ | 0.5 | — | — | Yes | OK |

[a]Added to 2.00 g of epoxy/polyol/SOC mixture.

The mixtures were also tested to evaluate the rate and extent of the polymerization of the mixtures during irradiation with visible light using the test procedures of Example 12. The photopolymerization characteristics are set forth in Table 4:

TABLE 4

Photocalorimetry Data for Spiroorthocarbonate/Epoxy/Polyol Mixtures

| Sample No. | ΔHphoto (J/g) | Ind. time (sec) | Time to max. (sec) | Conv. at peak (%) | Rate const. k (min$^{-1}$) |
|---|---|---|---|---|---|
| 1 | 189.4 | 41.6 | 78 | 28.1 | 6.32 ± 0.39 |
| 2 | 331.9 | 14.6 | 22 | 25.9 | 9.54 ± 0.53 |
| 3 | 129.4 | 125.4 | 202.8 | 17.9 | 0.37 ± 0.03 |
| 4 | 678 | 49.9 | 56.6 | 14.7 | 16.8 ± 2.7 |
| 5 | 184.3 | 40.7 | 62.8 | 22 | 5.12 ± 0.10 |
| 6 | 142.7 | 30 | 46.2 | 14.9 | 1.30 ± 0.33 |
| 7 | 53.4 | 35.3 | 78 | 19.1 | 0.51 ± 0.02 |
| 8 | 129.2 | 47.4 | 80.8 | 18.4 | 1.11 ± 0.19 |
| 9 | 85.3 | 82 | 142.2 | 17.3 | 0.23 ± 0.06 |
| 10 | 116.2 | 120.4 | 171.6 | 12.8 | 0.16 ± 0.03 |
| 11 | 671.7 | 34.2 | 45.6 | 31 | 12.50 ± 0.86 |
| 12 | 101.9 | 49.9 | 78.8 | 23.9 | 2.40 ± 0.13 |
| 13 | 526.3 | 42.9 | 70.4 | 37.9 | 2.60 ± 5.3 |
| 14 | 233.6 | 32.0 | 54.0 | 17.8 | 3.24 ± 0.37 |
| 15 | 130.8 | 39.5 | 64.0 | 22.2 | 4.79 ± 0.46 |

Having thus described the invention, what is claimed is:

1. A compound of the formula:

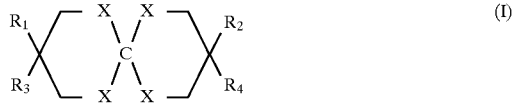

wherein
X=O or S;
$R_1$ and $R_2$ are independently selected from the group consisting of H, alkyl, aryl, substituted alkyl, and substituted aryl;
$R_3$ and $R_4$=—$(CH_2)_n$—O—$R_5$;
n=1 or 2;

$R_5$=alkyl, aryl, substituted aryl, substituted alkyl,

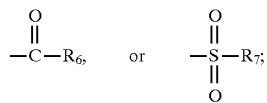

$R_6$=H, alkyl, aryl, substituted alkyl, or substituted aryl; and
$R_7$=alkyl, aryl, substituted alkyl, or substituted aryl.

2. The compound of claim 1, wherein $R_1$ and $R_2$ are ethyl and $R_3$ and $R_4$ are —$CH_2OCOCH_3$.

3. The compound of claim 1, wherein $R_1$ and $R_2$ are methyl and $R_3$ and $R_4$ are —$CH_2OCH_2C_6H_5$.

4. The compound of claim 1, wherein $R_1$ and $R_2$ are phenyl and $R_3$ and $R_4$ are —$CH_2OOCCH_3$.

5. The compound of claim 1, wherein $R_1$ and $R_2$ are methyl and $R_3$ and $R_4$ are —$CH_2OOCCH_3$.

6. The compound of claim 1, wherein $R_1$ and $R_2$ are ethyl and $R_3$ and $R_4$ are —$CH_2OOCCH_2CH_3$.

7. The compound of claim 1, wherein $R_1$ and $R_2$ are ethyl and $R_3$ and $R_4$ are —$CH_2OSOOCH_2CH_2CH_3$.

8. A polymeric composition comprising a cationic initiated reaction product of:
a spiroorthocarbonate compound,
a cationically polymerizable epoxy resin, and
a hydroxyl-containing material;
said spiroorthiocarbonate compound comprising one or more compounds of the formula:

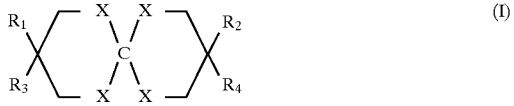

wherein
X=O or S;
$R_1$ and $R_2$ are independently selected from the group consisting of H, alkyl, aryl, substituted alkyl, and substituted aryl;

$R_3$ and $R_4$=—$(CH_2)_n$—O—$R_5$;
n=1 or 2;
$R_5$=alkyl, aryl, substituted aryl, substituted alkyl,

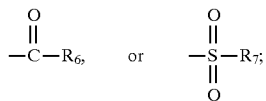

$R_6$=H, alkyl, aryl, substituted alkyl, or substituted aryl; and $R_7$=alkyl, aryl, substituted alkyl, or substituted aryl.

9. The composition of claim 8, wherein the hydroxyl-containing material is selected from the group consisting of polyoxyethylene glycols, polyoxypropylene glycols, polytetramethylene oxide glycols, hydroxyethylated cellulose, hydroxypropylated cellulose, hydroxy-terminated polyesters, hydroxy-terminated polyactones, ethoxylated bis-phenol A and hydroxy-terminated polyalkadienes.

10. The composition of claim 8, wherein said hydroxyl-containing material is selected from the group consisting of 3,4-epoxycyclohexanemethyl-3,4-epoxycyclohexane carboxylate, bis(3,4-epoxycyclohexylmethyleneoxy) adipate, and vinyl cyclohexene dioxide.

11. A dental composite comprising:
    a matrix comprising a cationic initiated reaction product of a spiroorthocarbonate compound, a cationically polymerizable epoxy resin, and a hydroxyl-containing material; and
    a dental filler material dispersed in said matrix in an amount of between about 10 to 90% by weight based on the total weight of the composite,
    said spiroorthocarbonate compound comprising one or more compounds of the formula:

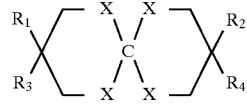

wherein
X=O or S;
$R_1$ and $R_2$ are independently selected from the group consisting of H, alkyl, aryl, substituted alkyl, and substituted aryl;
$R_3$ and $R_4$=—$(CH_2)_n$—O—$R_5$;
n=1 or 2;
$R_5$=alkyl, aryl, substituted aryl, substituted alkyl,

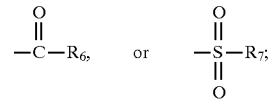

$R_6$=H, alkyl, aryl, substituted alkyl, or substituted aryl; and $R_7$=alkyl, aryl, substituted alkyl, or substituted aryl.

* * * * *